United States Patent
Perovitch et al.

(10) Patent No.: US 9,801,815 B2
(45) Date of Patent: Oct. 31, 2017

(54) GALENICAL FORM FOR THE ADMINISTRATION OF TRIPTANS BY BUCCAL TRANSMUCOUS MEANS

(76) Inventors: Philippe Perovitch, Le Temple (FR); Marc Maury, Saint Medard En Jalles (FR)

( * ) Notice: Subject to any disclaimer, the term of this patent is extended or adjusted under 35 U.S.C. 154(b) by 234 days.

(21) Appl. No.: 12/863,633

(22) PCT Filed: Jan. 29, 2009

(86) PCT No.: PCT/FR2009/050134
§ 371 (c)(1),
(2), (4) Date: Jul. 20, 2010

(87) PCT Pub. No.: WO2009/095621
PCT Pub. Date: Aug. 6, 2009

(65) Prior Publication Data
US 2010/0298401 A1    Nov. 25, 2010

(30) Foreign Application Priority Data

Jan. 30, 2008 (FR) ...................... 08 50571

(51) Int. Cl.
*A61K 9/00* (2006.01)
*A61K 9/08* (2006.01)
*A61K 31/404* (2006.01)

(52) U.S. Cl.
CPC ............. *A61K 9/006* (2013.01); *A61K 9/08* (2013.01); *A61K 31/404* (2013.01)

(58) Field of Classification Search
USPC ........................................ 424/400
See application file for complete search history.

(56) References Cited

U.S. PATENT DOCUMENTS

2010/0022496 A1    1/2010    Perovitch et al.

FOREIGN PATENT DOCUMENTS

| EP | 0321870 | * | 6/1989 |
| WO | 2005/032518 A1 | | 4/2005 |
| WO | 2008/035020 A2 | | 3/2008 |

OTHER PUBLICATIONS

Spierings et al. (Arch Neurol. 2001;58:944-950).*
Fuseau (Clin Pharmacokinet 2002; 41 (11): 801-811).*
International Search Report, dated Jul. 7, 2009, from corresponding PCT application.

* cited by examiner

*Primary Examiner* — Devang Thakor
(74) *Attorney, Agent, or Firm* — Young & Thompson

(57) ABSTRACT

A galenical form for the buccal transmucous administration of at least one active ingredient of the triptan family, includes at least:
  the active ingredient in basic form and in salt form, and
  a hydro-alcoholic solution that titrates at least 15 degrees of alcohol, whereby the active ingredient is present in a stable and complete state of dissolution in the hydro-alcoholic solution so as to allow a fast absorption of the active ingredient through the mucous membranes of the buccal cavity and/or the oropharynx. A process for the production of this galenical formulation as well as its use are described.

17 Claims, No Drawings

GALENICAL FORM FOR THE ADMINISTRATION OF TRIPTANS BY BUCCAL TRANSMUCOUS MEANS

FIELD OF THE INVENTION

This invention relates to a galenical form for the instantaneous systemic administration by buccal transmucous means of at least one active ingredient that belongs to the family of triptans, in particular Sumatriptan.

The invention also relates to a process for the production of this galenical form and to its use.

BACKGROUND OF THE INVENTION

Triptans are pharmaceutical active ingredients that are used for the treatment of migraine attacks, in particular acute Cluster Headache that represents a true therapeutic emergency.

Sumatriptan is the major anti-migraine pharmaceutical agent and the reference pharmaceutical agent on the market, but all triptans have the same physico-chemical nature and the same mode of central vascular action. In particular, Zolmitriptan, Almotriptan, Eletriptan, Naratriptan and Frovatriptan are known.

The triptans have the capacity to stimulate certain receptors of serotonin and more specifically the vascular receptors with 5-hydroxytryptamine 1 (5-HT1). The stimulation of these receptors causes central vasoconstriction reducing the vasodilatation phenomena and edema at the origin of the VAF attack.

It is known that triptans can be administered intravenously by drip, but this route has remained experimental because of the difficulty of its current therapeutic application, although such an administration has demonstrated a very short delay in effective clinical response for a very low dose that is administered.

Actually, this method of administration, requiring dedicated personnel and the use of specific equipment, has a high cost, is cumbersome for the patient who is subjected to hospitalization, and is not suitable for the treatment of migraine attacks. Consequently, although the benefits of the intravenous administration of triptans have been clinically evaluated and are extremely satisfactory, commercial use of these intravenous, specific galenical forms has never been undertaken.

With the attacks being unpredictable, certain patients need daily treatment, so that only self-administration is possible.

There are currently several methods for self-administration of triptans.

A first known method is the administration in the form of tablets.

Nevertheless, the triptans that are administered enterally do not work for about two hours, an excessive delay for any suffering patient who is waiting.

When they are introduced into the alimentary canal and the stomach, these active ingredients undergo the so-called "first digestive pass" effect, alterations and losses linked to the stomach environment or to variations of intestinal physiologies, including gastric stasis, paralysis thoroughly described as constant in the individuals suffering from migraines, which reduces the absorption of any active ingredient by at least 50%.

They are then subjected to a so-called "first hepatic pass" effect, which causes their more or less intense metabolization and/or their degradation, with the composition of numerous metabolites, for the most part inactive or toxic, causing secondary effects.

The dose of truly bioavailable active ingredient is therefore extremely small: only one very residual part of the quantity that is administered remains valid for producing the expected pharmacological effect.

Thus, by way of example, administered via the digestive tract, Sumatriptan has a residual bioavailability that is reduced to less than 14% of the administered dose, simultaneously with a mean volume of theoretical distribution in the human body of 200 liters and a half-life of 2 hours only when the maximum plasmatic concentration is reached only after 1 to 1.5 hours.

It is also known that the onset of a clinical effect on the ailment on average begins only 30 minutes after intake.

Actually, there are two major problems.

The first problem is that it is necessary to administer a sufficient dose of triptan to the patient, taking into account the weight status of the subject, the absorption, the metabolization, the dilution and the dispersion of this active ingredient in the organism, so that the sole active residual part reaches the vascular receptors with 5-hydroxytryptamine 1 (5-HT1) and produces pharmacological effectiveness.

The second is the fixed latency period linked to absorption, to metabolization, and to the diffusion of the active ingredient in the organism before the molecule acts and of which the patient perceives the beneficial effects.

The administration of triptans using tablets via the digestive tract is therefore suitable neither in rapidly effective treatment of migraines nor in the emergency of a cataclysmic headache such as acute Cluster Headache.

Other possible means for self-administration of triptans, such as the buccal permucous means, the nasal permucous means, and the subcutaneous injectable means, are also known.

The buccal permucous means makes it possible to administer medications by passive passage of sublingual, jugal, gingival, lingual, palatal, or pharyngeal mucous membranes, and then passage into the sublingual veins and cardiac distribution, and with general circulation, thus short-circuiting the digestive passage and the hepatic metabolism.

Nevertheless, the existing formulations, such as the orodispersible Zolmitriptan tablets, are not satisfactory, in particular because of the fact that the triptans are by nature insoluble in biological liquids such as saliva. For these forms, if their dispersibility is oral, the insoluble active ingredient is then swallowed and undergoes the same kind of digestive metabolism as that of the triptan forms in tablets, which shows the equivalence of bioavailability claimed by these two forms—orodispersible and tablet—in their legal notes.

This is also the case of sprays and chewable gelatin capsules that are designed for a transmucous administration, described in the application WO-2005/032518. These formulations have characteristics that are not satisfactory in terms of precision of administration, absorption yields and ensured bioavailability of administered dosages.

It is a matter of complex liquid formulations that comprise a combination of multiple ingredients designed to solubilize and stabilize Sumatriptan molecules, in particular propylene glycol, polyethylene glycol, benzoic acid, etc., and to create a very specific state of viscosity for a spray distribution. During administration, the distribution in the buccal cavity nevertheless remains diffuse and random, and upon reception of the spray-propelled particles, the latter are instantaneously mixed with the saliva that is produced in a reflexive and mechanical manner in the buccal cavity. This mixture is generally swallowed automatically by the patient before the active ingredient has had the opportunity to pass through the buccal mucous membranes to pass into the venous vascular stream. Only a very small fraction of the formulated active ingredient is therefore directly available by permucous passage, around 20 to 25% of the administered unit dose, and the effectiveness also remains very far from that obtained by intravenous or subcutaneous means.

The nasal method makes possible a permucous absorption of the active ingredient by spraying a liquid form (spray). In the field of anti-migraine agents, in particular nasal sprays that consist of basic Sumatriptan in aqueous solution with 4 vehicles are known (Imigrane). If this nasal means has shown a dose/effect yield that is slightly better than the enteric means, the maximum concentration of Sumatriptan is evaluated between 13.1 and 14.14 ng/ml of plasma 30 minutes after the administration of a single intra-nasal dose of 20 mg. The mean bioavailability of the administered dose is therefore not greater than 10%. This inadequate yield is also always random because of the possible occupancy of nasal passages by mucus. Thus, these formulations for administration via the nasal passages are no longer satisfactory.

There is also another method of administration that was developed twenty years ago for Sumatriptan: the subcutaneous injectable pathway, when administered by doctor or nurse or by self-injection. Studies have shown that the subcutaneous injection of Sumatriptan with a single dosage of 6 mg produces 75% of remission of the acute Cluster Headache attack in a mean delay of 15 minutes.

However, this method of administration, which represents a high unit cost, requires the use of a specific piece of equipment, a self-injecting device; even for a patient in a true attack, it proves to be not very ergonomic, and it is painful and much more invasive than the simple intake of tablets or the use of a spray.

In addition, although the exclusive form of self-administration is the most effective that currently exists for treatment of the attack, it still remains very far from the effectiveness obtained by intravenous means that produces 90% of remissions after 3 to 4 minutes.

SUMMARY OF THE INVENTION

There is therefore a need for a galenical formulation that is simple to use, less expensive, readily available and not very invasive, making it possible to administer an immediately bioavailable amount of triptan so as to be able to very quickly and effectively treat the painful symptoms or the debilitating problems of migraine attacks.

This is the purpose of this invention by proposing a very specific galenical form that makes it possible to ensure the instantaneous administration by buccal transmucous means of at least one active ingredient of the triptan family, comprising at least:
    Said active ingredient in basic form and in salt form, and
    An hydro-alcoholic solution that titrates at least 15 degrees of alcohol, whereby said active ingredient is present in a stable and complete state of dissolution in the hydro-alcoholic solution.

The invention also proposes a process for preparation as well as the use of this formulation for the treatment or the prevention of painful symptoms or debilitating problems of migraine attacks.

Advantageously, the formulation according to the invention makes possible the instantaneous and complete permucous passage of a therapeutic preparation based on triptans by limiting any salivary dilution and swallowing of the triptan molecules that are delivered almost instantaneously to the vascular system for a distribution of the entire dosage to cerebral receptors 5-HT1 of serotonin.

Other characteristics and advantages will emerge from the following description of the invention.

According to a first aspect, the invention therefore has as its object a formulation for the administration by buccal trans-mucous means of at least one active ingredient of the triptan family, comprising at least:
    Said active ingredient in basic form and in salt form, and
    An hydro-alcoholic solution that titrates at least 15 degrees of alcohol, whereby said active ingredient is present in a stable and complete state of dissolution in the hydro-alcoholic solution so as to make possible a rapid absorption of said active ingredient through the mucous membranes of the buccal cavity. "Buccal transmucous means" is defined as any passive passage of a lipophilic or amphiphilic molecule through the lingual, sublingual, gingival, palatal, or jugal mucous membranes, or any other mucous membranes that constitute the buccal cavity.

"Stable and complete dissolution state" defines a state of dissolution that restores the active ingredient to the molecular and weakly ionized state in its dissolution environment, whereby the state of dissolution prevents any eventuality of an inopportune recrystallization.

"Hydro-alcoholic solution that titrates X degrees of alcohol" is defined as a solution that has a degree of alcohol of X, corresponding to the ratio between the volume of pure alcohol (100°) that is contained in the dilute-alcoholic solution, and the total volume of this solution. The degree of alcohol of the hydro-alcoholic solution varies based on the degree of alcohol that is used to form the solution and the water/alcohol ratio of the solution. For example, for an initial alcohol at 100 degrees and a water/alcohol ratio of 50/50, the hydro-alcoholic solution titrates 50 degrees of alcohol.

The active ingredient of the triptan family is present in basic form and in salt form, for example in the form of succinate, chlorohydrate, or sulfate. Preferably, the active ingredient is present between 5 and 95% in basic form and between 5 and 95% in salt form. Still more preferably, the active ingredient is present between 5 and 40% in basic form and between 60 and 95% in salt form.

According to a particularly suitable embodiment, the active ingredient is Sumatriptan.

DETAILED DESCRIPTION OF THE INVENTION

Preferably, the galenical form according to the invention comes in the form of an hydro-alcoholic solution that comprises between 15 and 85% alcohol by mass and a water content of between 15 and 85% by mass. Still more preferably, the formulation according to the invention comes in the form of an hydro-alcoholic solution that comprises between 30 and 85% of alcohol by mass and a water content of between 15 and 70% by mass.

The hydro-alcoholic solution has a variable degree of alcohol of at least 15 degrees, preferably between 15 and 95 degrees, still more preferably between 20 and 70 degrees, and ideally around 45 degrees. Advantageously, the hydro-alcoholic solution is the sole solvent used in the formulation according to the invention.

In addition, the alcohol of the hydro-alcoholic solution does not only play the role of diluent, but also that of promoter of an accelerated permucous absorption, whose speed increases based on the elevation of the degree of alcohol used.

According to a preferred embodiment of the invention, the hydro-alcoholic solution is produced with a water and ethanol base.

By way of illustration, the dissolution coefficient of Sumatriptan in ethanol makes it possible to obtain a complete dissolution of said active ingredient at a level of 2 mg, 4 mg or 6 mg of Sumatriptan for 0.75 ml of ethanol at 35%. This coefficient can be modulated based on the degree of alcohol and the water/ethanol ratio that is used.

The galenical form according to the invention can also comprise a pH-correcting agent.

A pH-correcting agent is defined as any acidic agent or any basic agent that does not alter the physico-chemical natures of the active ingredient(s).

Preferably, the pH-correcting agent is selected from among the sodium carbonates and bicarbonates, the monosodium or disodium phosphates, the triethanolamine, soda (NaOH) and potash (KOH) but also agents of hydrochloric acid, sulfuric acid, phosphoric acid, citric acid, malic acid, lactic acid, succinic acid and/or butyric acid.

Preferably, the pH of the formulation according to the invention is between 4.0 and 9.0, and even more preferably between 4.0 and 8.0.

The galenical form according to the invention makes it possible for the active ingredient to passively pass through the buccal mucous membranes in a delay that is less than 30 seconds after administration. This very fast absorption period makes it possible to prevent any stagnation of the solution and the active ingredient in the buccal atmosphere as well as their ill-timed mixing with the saliva that can alter them, which would introduce a break in the continuity and the stability of the dissolution of the active ingredient(s). This short delay also makes it possible to prevent any reflex swallowing of the solution and the active ingredient that it contains.

The buccal trans-mucous passage of the active ingredient that is presented in a state of dissolution according to the invention on the side of the outside epithelial membrane, consisting of phospholipidic structures that passively absorb the lipophilic molecules by elective affinity, is based on an osmotic demand toward the other side of said membrane, in which the concentration of the dissolved active ingredient and that of the alcoholic solution being considered participate together. The osmotic flow is all the more enduring and powerful since the degree of alcohol that serves as absorption promoter is high. In the particular case of Sumatriptan, according to the invention, a suitable degree of alcohol is between 15° and 95°, preferably between 20° and 70°. This makes it possible to ensure simultaneously obtaining and adjusting the best coefficient of dissolution and stabilization of Sumatriptan as well as the promotion of its permucous passage in a delay of about ten seconds. One particularly suitable embodiment corresponds to 0.75 ml of hydro-alcoholic solution with a degree of alcohol of 45° for 2 mg, 4 mg, or 6 mg of Sumatriptan.

The mucous membranes of the mouth have a very dense, quasi-spongy network of microvessels, although the molecules, both of dissolved alcoholic solvent and active ingredient, which pass through the lipophilic pores of the epithelial membrane, are instantaneously captured by the blood micro-circulation and collected toward the sublingual veins and the floor and the whole veins draining the mucous floor of the mouth. This phenomenon is accentuated by the presence of the alcohol that causes a vasodilatation and an increase in the local microvascular flow rate of the mucous membranes.

Because of this elevated circulatory flow rate, locally increased by alcohol, there is therefore never equilibrium on either side of the membrane; the concentration in the mouth remains ever higher until the mechanism is exhausted when there are no more molecules to be absorbed.

Thus, notoriously unlike all of the other so-called "sublingual" forms, all of the alcohol and the active ingredient that is dissolved according to the invention passes through the buccal mucous membrane within several seconds.

The use of the galenical form according to the invention makes it possible to passively administer a dose of triptan that is immediately absorbed as soon as it is deposited and upon contact with the mucous membrane to be distributed instantaneously vascularly, without any delay for its pharmacological action and without undergoing the major preliminary effects of the digestive and hepatic passages. The galenical form according to the invention therefore makes possible an immediacy of complete mucous tissue absorption of the triptan molecules, and then their distribution into the central circulation of the organism, generating a "flash"-type rapid pharmacological response.

For example, with a galenical form according to the invention that is produced from 2 mg of Sumatriptan that is solubilized in 0.75 ml of ethyl alcohol at 45°, it is possible to administer almost instantaneously and passively a very significant dose of Sumatriptan, 2 mg, which corresponds to the dose that is normally administered intravenously, or less than one twenty-fifth of the dose that is usually administered orally (50 mg).

The hydro-alcoholic solution that titrates at least 15° of alcohol according to the invention also offers the advantages of solubilizing the molecules of triptans even though they are lipophilic, which allows their spontaneous permucous absorption, and of protecting the pharmaceutical formulation with regard to a microbiological contamination without having to introduce (an) antimicrobial preservation agent(s).

Thus, the hydro-alcoholic solution according to the invention has four capabilities:
- It plays the role of solvent of the active ingredient of the family of triptans, lipophilic molecules of low molecular weight,
- It activates the permucous passage of this active ingredient that is dissolved as presented in the molecular state at the lipophilic membrane,
- The degree of alcohol doubly increases the speed of mucous membrane absorption by osmotic effect and by generating a reflexive microvascular vasodilatation, which accelerates the local microcirculatory flow rate, and
- It is its own stability agent, which prevents the use of conventional additives.

Advantageously, this invention offers a great simplicity of production and a very good galenical stability: the water/alcohol solution ensures the solubilization of the active ingredient while eliminating most of the vehicles that are used in the usual pharmaceutical forms. It therefore makes it possible both to reduce the production costs and to reduce the risks of intolerance and the possible interactions between active ingredient and vehicles.

Notably, the action times of the galenical form according to the invention are very short compared to the slowness of absorption of medications based on existing triptans designed for self-administration.

The almost-instantaneous pharmacological release makes it possible for a patient to administer to himself a product for an effect that is equivalent to the effectiveness of a flash intravenous injection of triptan into the circulatory system.

It involves a much better method of administration in terms of simplicity and availability of non-traumatic administration but also in terms of unit cost and therapeutic cost compared to all of the existing methods for administering triptans.

The gain in terms of the dose/effect ratio is considerable since no more than 4 to 8% of the reference dose by weight is used orally, or between 92 and 96% of the dose or less for a therapeutic effect that is immediately obtained in this case.

In addition, since the triptan molecules do not encounter any major obstacle to their instantaneous distribution in the cerebral arterial circulation that they achieve in several seconds, the basic administered dose is low, close to the useful dose for exerting the required pharmacological activity. This dose depends, of course, on the desired effect. It is preferably between 0.5 mg and 6 mg for Sumatripan, for administration volumes, i.e., volumes of dilute-alcohol solution, which are less than 5 ml, preferably varying from 0.5 ml to 1 ml.

Furthermore, with the buccal mucous membrane using an extremely large total absorption surface area, scaled down by its nature of folded, villous tissue, the administration of the galenical form according to the invention is free of any risk of ill-timed swallowing or swallowing the wrong way. Actually, it allows an extremely fast permucous passage that prevents any salivary dissolving or swallowing of the active ingredient that is administered, with the advantage of not destabilizing the mucous membranes, for example with surfactant derivatives, as it is the case of certain existing formulations with a "sublingual" purpose.

Likewise, the effects of alcohol are insignificant. By way of example, 0.75 ml of ethanol at 35° would only produce a blood alcohol level of less than 0.004 g per liter of blood, or $1/125^{th}$ of the legal tolerances in France of 0.5 g per liter.

A particularly suitable process for the production of the galenical form according to the invention comprises the following stages:
 Introducing into the alcohol at least one active ingredient from the family of triptans in basic form,
 Stirring the preparation until said active ingredient is completely dissolved,
 Adding purified water to the preparation, and then said active ingredient in the form of salt,
 Stirring the preparation until dissolution is complete, and
 Adding water if necessary to round out the desired volume.

According to a preferred embodiment, the process comprises the following stages:
 Introducing into the alcohol—while being stirred—at least one active ingredient from the family of triptans in basic form, preferably from basic Sumatriptan,
 Stirring the preparation, preferably for 10 to 60 minutes, until said active ingredient is completely dissolved,
 Adding purified water to the preparation, and then said active ingredient in the form of salt, preferably Sumatriptan succinate,
 Stirring the preparation, preferably for 10 to 60 minutes, until dissolution is complete,
 Adding water if necessary to round out the desired volume,
 Adding pH-correcting agents to obtain a physiologically compatible pH that is between 4.0 and 9.0, preferably between 4.0 and 8.0,
 Filtering the preparation, and
 Distributing the solute that is obtained in suitable containers of less than 5 ml of volume, preferably flasks made of brown glass or opaque polymer of 2 ml, ensuring the stability of the product.

This invention can be used for the instantaneous systemic administration at reduced and useful doses of triptan, in particular Sumatriptan.

In particular, the galenical form according to this invention can be used for the production of a medication for the treatment of migraines in general and VAF attacks in particular. Such a medication has an anti-migraine therapeutic activity in a very short time period and at very small doses relative to traditional doses.

The formulation according to the invention, corresponding to a very small liquid volume, is very easy to administer. A patient can easily place it in his mouth in direct contact with a specific mucous membrane zone, with a small surface area. Preferably, the patient is to place the formulation according to the invention in a mucous territory protected from salivary secretions, for example the jugal cradle, delimited, on the one hand, by the lower and external gums' crown mucous, and, on the other hand, by the lower cheeks' mucous surfaces and lips' internal mucous. This channel on average shows a closed reservoir of about 18 cm in length and 1 to 1.5 cm in depth, or a mucous absorption surface area of 35 to 55 $cm^2$.

According to a last aspect, the formulation according to the invention requires a specific industrial packaging so as to make possible its simple and ergonomic, protected use and to prevent the degradation of the active ingredient upon contact with the air.

One particular embodiment consists in using preferably small, opaque, plastic or flexible metalloplastic or glass packaging that is filled under inert atmosphere, such as nitrogen, for the protection of the stability of the composition and the impermeability to oxygen and to radiation. This packaging ensures the dissolution and the stability over time of active ingredients that are dissolved in hydro-alcoholic solution according to the invention.

Preferably, this packaging comprises a cannula that makes possible the precise placing of the solution according to the invention upon contact with a suitable mucous zone.

For comfort of use by the patient and for easy transport, it is preferably possible to resort to packages in the form of specific sealed cases. Even more preferably, the galenical form according to the invention is packaged in single-dose packages of 0.5 to 5 ml, able to provide a suitable dose of active ingredient.

Advantageously, this packaging is easy to transport and makes possible an easy use of the galenical form at any moment of the day.

It is possible to cite several examples of formulation of Sumatriptan according to the invention, with a volume of 0.75 ml, particularly suitable for producing effectiveness on the cerebral level in a delay of only several minutes:

Formulation 1:

| | |
|---|---|
| Sumatriptan: | 6.0 mg |
| Introduced in the form of: | |
| Basic Sumatriptan | 1.20 mg |
| Sumatriptan succinate | 6.72 mg |
| 95% (v/v) Ethyl alcohol: | 0.3 ml |
| Purified water: sufficient quantity for | 0.75 ml |

It should be noted that the quantity of Sumatriptan in 6.72 mg of Sumatriptan succinate is 4.8 mg.

This formulation example can be obtained by the implementation of the process that is described below for a lot of 1,000 doses, or 0.75 L.

Introduce 0.3 L of 95% (v/v) ethanol and 1.20 g of basic Sumatriptan into a stainless steel tank.

Using a stirring mechanism with a propeller, stir the preparation until the basic Sumatriptan is completely dissolved.

Add 0.450 L of purified water to the mixture, and then 6.72 g of Sumatriptan succinate.

Using a stirring mechanism with a propeller, stir the preparation until a homogeneous suspension and complete dissolution are achieved.

Filter the preparation on a polypropylene filter or the equivalent with a pore size of 5 μm and distribute the preparation into single-dose 0.75 ml flasks.

Formulation 2:

| Sumatriptan: | 4.0 mg |
| Introduced in the form of: | |
| Basic Sumatriptan | 0.8 mg |
| Sumatriptan succinate | 4.48 mg |
| 95% (v/v) Ethyl alcohol: | 0.3 ml |
| Purified water: sufficient quantity for | 0.75 ml |

It should be noted that the quantity of Sumatriptan in 4.48 mg of Sumatriptan succinate is 3.2 mg.

This formulation example can be obtained by the implementation of the process that is described below for a lot of 1,000 doses, or 0.75 L.

Introduce 0.3 L of 95% (v/v) ethanol and 0.8 g of basic Sumatriptan into a stainless steel tank.

Using a stirring mechanism with a propeller, stir the preparation until the basic Sumatriptan is completely dissolved.

Add 0.450 L of purified water to the mixture, and then 4.48 g of Sumatriptan succinate.

Using a stirring mechanism with a propeller, stir the preparation until a homogeneous suspension and complete dissolution are achieved.

Filter the preparation on a polypropylene filter or the equivalent with a pore size of 5 μm and distribute the preparation in single-dose 0.75 ml flasks.

Formulation 3:

| Sumatriptan: | 2.0 mg |
| Introduced in the form of: | |
| Basic Sumatriptan | 0.4 mg |
| Sumatriptan succinate | 2.24 mg |
| 95% (v/v) Ethyl alcohol: | 0.3 ml |
| Purified water: sufficient quantity for | 0.75 ml |

It should be noted that the quantity of Sumatriptan in 2.24 mg of Sumatriptan succinate is 1.6 mg.

This formulation example can be obtained by the implementation of the process that is described below for a lot of 1,000 doses, or 0.75 L.

Introduce 0.3 L of 95% (v/v) ethanol and 0.40 g of basic Sumatriptan into a stainless steel tank.

Using a stirring mechanism with a propeller, stir the preparation until the basic Sumatriptan is completely dissolved.

Add 0.450 L of purified water to the mixture, and then 2.24 g of Sumatriptan succinate.

Using a stirring mechanism with a propeller, stir the preparation until a homogeneous suspension and complete dissolution are achieved.

Filter the preparation on a polypropylene filter or the equivalent with a pore size of 5 μm and distribute the preparation into single-dose 0.75 ml flasks.

Formulation 4:

| Sumatriptan: | 1.0 mg |
| Introduced in the form of: | |
| Basic Sumatriptan | 0.20 mg |
| Sumatriptan succinate | 1.12 mg |
| 95% (v/v) Ethyl alcohol: | 0.3 ml |
| Purified water: sufficient quantity for | 0.75 ml |

It should be noted that the quantity of Sumatriptan in 1.12 mg of Sumatriptan succinate is 0.8 mg.

This formulation example can be obtained by the implementation of the process that is described below for a lot of 1,000 doses, or 0.75 L.

Introduce 0.3 L of 95% (v/v) ethanol and 0.20 g of basic Sumatriptan into a stainless steel tank.

Using a stirring mechanism with a propeller, stir the preparation until the basic Sumatriptan is completely dissolved.

Add 0.450 L of purified water to the mixture, and then 1.12 g of Sumatriptan succinate.

Using a stirring mechanism with a propeller, stir the preparation until a homogeneous suspension and complete dissolution are achieved.

Filter the preparation on a polypropylene filter or the equivalent with a pore size of 5 μm and distribute the preparation into single-dose 0.75 ml flasks.

Formulation 5:

| Sumatriptan: | 1.0 mg |
| Introduced in the form of: | |
| Basic Sumatriptan | 0.20 mg |
| Sumatriptan succinate | 1.12 mg |
| 95% (v/v) Ethyl alcohol: | 0.3 ml |
| Purified water: sufficient quantity for | 0.75 ml |
| Sodium hydroxide: sufficient quantity for | pH 7.5 |

It should be noted that the quantity of Sumatriptan in 1.12 mg of Sumatriptan succinate is 0.8 mg.

This formulation example can be obtained by the implementation of the process that is described below for a lot of 1,000 doses, or 0.75 L.

Introduce 0.3 L of 95% (v/v) ethanol and 0.20 g of basic Sumatriptan into a stainless steel tank.

Using a stirring mechanism with a propeller, stir the preparation until the basic Sumatriptan is completely dissolved.

Add 0.450 L of purified water to the mixture, and then 1.12 g of Sumatriptan succinate.

Using a stirring mechanism with a propeller, stir the preparation until a homogeneous suspension and complete dissolution are achieved.

Add sodium hydroxide to adjust the pH of the solution to 7.5.

Filter the preparation on a polypropylene filter or the equivalent with a pore size of 5 μm and distribute the preparation into single-dose 0.75 ml flasks.

Formulation 6:

| Sumatriptan:<br>Introduced in the form of: | 0.75 mg |
|---|---|
| Basic Sumatriptan | 0.15 mg |
| Sumatriptan succinate | 0.84 mg |
| 95% (v/v) Ethyl alcohol: | 0.3 ml |
| Purified water: sufficient quantity for | 0.75 ml |

It should be noted that the quantity of Sumatriptan in 0.84 mg of Sumatriptan succinate is 0.60 mg.

This formulation example can be obtained by the implementation of the process that is described below for a lot of 1,000 doses, or 0.75 L.

Introduce 0.3 L of 95% (v/v) ethanol and 0.15 g of basic Sumatriptan into a stainless steel tank.

Using a stirring mechanism with a propeller, stir the preparation until the basic Sumatriptan is completely dissolved.

Add 0.450 L of purified water to the mixture, and then 0.84 g of Sumatriptan succinate.

Using a stirring mechanism with a propeller, stir the preparation until a homogeneous suspension and complete dissolution are achieved.

Filter the preparation on a polypropylene filter or the equivalent with a pore size of 5 μm and distribute the preparation into single-dose 0.75 ml flasks.

Formulation 7:

| Sumatriptan:<br>Introduced in the form of: | 0.50 mg |
|---|---|
| Basic Sumatriptan | 0.10 mg |
| Sumatriptan succinate | 0.56 mg |
| 95% (v/v) Ethyl alcohol: | 0.3 ml |
| Purified water: sufficient quantity for | 0.75 ml |

It should be noted that the quantity of Sumatriptan in 0.56 mg of Sumatriptan succinate is 0.4 mg.

This formulation example can be obtained by the implementation of the process that is described below for a lot of 1,000 doses, or 0.75 L.

Introduce 0.3 L of 95% (v/v) ethanol and 0.10 g of basic Sumatriptan into a stainless steel tank.

Using a stirring mechanism with a propeller, stir the preparation until the basic Sumatriptan is completely dissolved.

Add 0.450 L of purified water to the mixture, and then 0.56 g of Sumatriptan succinate.

Using a stirring mechanism with a propeller, stir the preparation until a homogeneous suspension and complete dissolution are achieved.

Filter the preparation on a polypropylene filter or the equivalent with a pore size of 5 μm and distribute the preparation into single-dose 0.75 ml flasks.

Formulation 8:

| Sumatriptan:<br>Introduced in the form of: | 0.25 mg |
|---|---|
| Basic Sumatriptan | 0.05 mg |
| Sumatriptan succinate | 0.28 mg |
| 95% (v/v) Ethyl alcohol: | 0.4 ml |
| Purified water: sufficient quantity for | 0.75 ml |

It should be noted that the quantity of Sumatriptan in 0.25 mg of Sumatriptan succinate is 0.2 mg.

This formulation example can be obtained by the implementation of the process that is described below for a lot of 1,000 doses, or 0.75 L.

Introduce 0.4 L of 95% (v/v) ethanol and 0.05 g of basic Sumatriptan into a stainless steel tank.

Using a stirring mechanism with a propeller, stir the preparation until the basic Sumatriptan is completely dissolved.

Add 0.450 L of purified water to the mixture, and then 0.28 g of Sumatriptan succinate.

Using a stirring mechanism with a propeller, stir the preparation until a homogeneous suspension and complete dissolution are achieved.

Filter the preparation on a polypropylene filter or the equivalent with a pore size of 5 μm and distribute the preparation into single-dose 0.75 ml flasks.

Formulation 9:

| Sumatriptan:<br>Introduced in the form of: | 2.00 mg |
|---|---|
| Basic Sumatriptan | 1.6 mg |
| Sumatriptan succinate | 0.56 mg |
| 95% (v/v) Ethyl alcohol: | 0.4 ml |
| Purified water: sufficient quantity for | 0.75 ml |
| Sodium bicarbonate: sufficient quantity for | pH 7.5 |

It should be noted that the quantity of Sumatriptan in 0.56 mg of Sumatriptan succinate is 0.4 mg.

This formulation example can be obtained by the implementation of the process that is described below for a lot of 1,000 doses, or 0.75 L.

Introduce 0.4 L of 95% (v/v) ethanol and 1.6 g of basic Sumatriptan into a stainless steel tank.

Using a stirring mechanism with a propeller, stir the preparation until the basic Sumatriptan is completely dissolved.

Add 0.450 L of purified water to the mixture, and then 0.56 g of Sumatriptan succinate.

Using a stirring mechanism with a propeller, stir the preparation until a homogeneous suspension and complete dissolution are achieved.

Add sodium bicarbonate to adjust the pH of the solution to 7.5.

Filter the preparation on a polypropylene filter or the equivalent with a pore size of 5 μm and distribute the preparation into single-dose 0.75 ml flasks.

A pilot study was conducted to evaluate the clinical effectiveness in particular of formulations 2 and 3 against the acute Cluster Headache attack.

The study was conducted on 23 patients.

Formulations 2 and 3 of the examples were administered to patients.

The total remission of the acute Cluster Headache attack, complete sedation of the pathology, was achieved on average in 43.5% of patients after 20 minutes. The results obtained in remission percentage at 20 minutes are presented in the table below:

| | % Remission at 20 Minutes |
|---|---|
| Formulation 2 (4 mg) | 60.0% |
| Formulation 3 (2 mg) | 41.7% |

It is noted that the most significant remissions at 20 minutes are achieved with the 4 mg (60%) dose. In addition, the 2 mg dose makes it possible in less than 20 minutes to reach almost the remission level of the nasal solute Imigrane with 20 mg after 2 hours.

Furthermore, the evaluation of the pain in patients who have severe pain is presented in the table below:

|  | % Severe Pain at T0 | % Severe Pain at T20 Minutes | Absolute Severe Pain Reduction | Relative Severe Pain Reduction |
| --- | --- | --- | --- | --- |
| Formulation 2 (4 mg) | 100% | 20% | −80% | −80% |
| Formulation 3 (2 mg) | 50% | 50% | −42% | −84% |

It is noted that the best reduction of pain is achieved for the 4 mg dosage that makes it possible to reduce the patient's pain by 80%.

The study has also made it possible to evaluate the percentage of patients who no longer have any pain or have slight pain 20 minutes after the administration:

|  | % No Pain or Slight Pain After 20 Minutes |
| --- | --- |
| Formulation 2 (4 mg) | 60.0% |
| Formulation 3 (2 mg) | 58% |

In addition, no secondary effect was observed.

Of course, the invention obviously is not limited to the examples that are shown and described above, but on the contrary covers all of the variants.

The invention claimed is:

1. A galenical form for buccal transmucous administration of at least one active ingredient of the triptan family, comprising:
    said active ingredient in a combination of a basic form and a salt form, and
    a solvent, said solvent consisting of a hydro-alcoholic solution of water and ethanol, the water content being between 15% and 70% by mass and the ethanol content being between 30% and 85% by mass, said hydro-alcoholic solution being the sole solvent,
    wherein the galenical form contains between 0.5 and 6 mg of said active ingredient in less than 5 ml of the solvent, and
    whereby said active ingredient is present in a stable and complete state of dissolution in the solvent so as to allow fast absorption of all of said active ingredient through mucous membranes of a buccal cavity, wherein the mucous membranes are the gingival and/or jugal mucous membranes.

2. The galenical form according to claim 1, wherein the active ingredient is present in an amount of between 5 and 95% by mass in the basic form and between 5 and 95% by mass in the salt form.

3. The galenical form according to claim 1, wherein the active ingredient is present in an amount of between 5 and 40% by mass in the basic form and between 60 and 95% by mass in the salt form.

4. The galenical form according to claim 1, wherein the salt form of the at least one active ingredient is the form of a succinate, chlorhydrate, or sulfate of said active ingredient.

5. The galenical form according to claim 1, wherein the at least one active ingredient is Sumatriptan.

6. The galenical form according to claim 1, further comprising a pH-correcting agent.

7. The galenical form according to claim 6, wherein the pH-correcting agent is one or more selected from the group consisting of: sodium carbonates and bicarbonates, monosodium or disodium phosphates, triethanolamine, soda, potash, hydrochloric acid, sulfuric acid, succinic acid, butyric acid, phosphoric acid, citric acid, malic acid and lactic acid.

8. The galenical form according to claim 1, wherein the pH is between 4.0 and 9.0.

9. A process for obtaining the galenical form of claim 1, which comprises the following stages:
    introducing into the ethanol at least one active ingredient from the triptan family in basic form,
    stirring the preparation until said active ingredient is completely dissolved,
    adding purified water to the preparation, and then said active ingredient in the form of a salt,
    stirring the preparation until dissolution is complete, and
    adding water as necessary to round out the desired volume.

10. The process according to claim 9, further comprising:
    introducing basic sumatriptan into the alcohol while being stirred,
    stirring the preparation for 10 to 60 minutes, until said active ingredient is completely dissolved,
    adding purified water to the preparation, and then sumatriptan succinate,
    stirring the preparation for 10 to 60 minutes, until dissolution is complete,
    adding water as necessary to round out the desired volume,
    adding pH-correcting agents to obtain a physiologically compatible pH of between 4.0 and 9.0,
    filtering the preparation, and
    distributing the solute that is obtained in suitable containers having a volume of less than 5 ml.

11. The galenical form according to claim 1, comprising 0.5-6 mg of sumatriptan per 0.5-1 ml of the solvent.

12. A pharmaceutical composition for treating a migraine attack, comprising:
    sumatriptan, in a combination of a basic form and a salt form; and
    a solvent, said solvent consisting of a hydro-alcoholic solution of water and ethanol, the water content being between 15%-70% by mass and the ethanol content being between 30%-85% by mass, the hydro-alcoholic solution being the sole solvent of the sumatriptan,
    wherein the composition is in a form for buccal transmucous administration to a subject and comprises 0.1-6 mg sumatriptan per ml solvent.

13. The pharmaceutical composition according to claim 12, wherein a single dose of the composition comprises 0.5-6 mg of sumatriptan.

14. The pharmaceutical composition according to claim 13, wherein the single dose comprises 0.5-1 ml of the solvent.

15. The pharmaceutical composition according to claim 12, wherein the composition comprises 0.33-1.33 mg sumatriptan per ml of solvent.

16. The pharmaceutical composition according to claim 12, wherein the sumatriptan is present in an amount of 5-40% by mass in the basic form and 60-95% by mass in the salt form, with respect to the total mass of sumatriptan.

17. The pharmaceutical composition according to claim 12, wherein the sumatriptan is present in a stable and complete state of dissolution in the solvent so as to allow absorption of all of the sumatriptan through the gingival and/or jugal mucous membranes of a buccal cavity.

* * * * *